United States Patent [19]
Fishman

[11] Patent Number: 5,119,803
[45] Date of Patent: Jun. 9, 1992

[54] DISPOSABLE MEDICINAL APPLICATOR AND GUM MASSAGE TIP

[76] Inventor: John Fishman, 515 Dadeland Medical Bldg., 7400 N. Kendall Dr., Miami, Fla. 33156

[21] Appl. No.: 709,202

[22] Filed: Jun. 3, 1991

Related U.S. Application Data

[63] Continuation-in-part of Ser. No. 563,691, Aug. 6, 1990, Pat. No. 5,044,356.

[51] Int. Cl.$^5$ .................... A61H 7/00; A61G 17/02
[52] U.S. Cl. .................... 128/62 A; 433/80
[58] Field of Search ............ 128/62 A; 433/80; 132/329

[56] References Cited

U.S. PATENT DOCUMENTS

| | | | |
|---|---|---|---|
| 3,563,233 | 2/1971 | Bodine | 128/62 A |
| 3,636,947 | 1/1972 | Balamuth | 128/66 |
| 4,577,649 | 3/1986 | Shimenkov | 132/93 |
| 4,628,564 | 12/1986 | Youssef | 15/167 R |
| 4,653,480 | 3/1987 | Rabinowitz | 128/62 A |
| 4,748,709 | 6/1988 | Oates | 15/104.93 |
| 4,831,676 | 5/1989 | Denmark | 15/104.93 |
| 4,880,382 | 11/1989 | Moret et al. | 433/118 |
| 4,909,241 | 3/1990 | Burn et al. | 128/62 A |
| 5,044,356 | 9/1991 | Fishman et al. | 128/62 A |

Primary Examiner—Gene Mancene
Assistant Examiner—Cindy A. Cherichetti
Attorney, Agent, or Firm—Malloy, Downey & Malloy

[57] ABSTRACT

A disposable medicinal applicator tip of the type for use on a handheld gum massaging tool, the applicator tip being specifically adapted to carry a charge of medicament so that when the tip is moved over the gum area, the gums are massaged while the tip simultaneously delivers the medicament to the gums and surrounding area providing necessary topical treatment at the sight of gum disease.

3 Claims, 1 Drawing Sheet

DISPOSABLE MEDICINAL APPLICATOR AND GUM MASSAGE TIP

This is a continuation-in-part application of presently co-pending application Ser. No. 07/563,691 filed on Aug. 6, 1990 now Pat. No. 5,044,356.

BACKGROUND OF THE INVENTION

1. Field of the Invention

The present invention relates generally to a disposable gum massage tip adapted for use on a handheld dental tool and more specifically to a disposable gum massage tip adapted to carry a charge of medicament for topical application to the gums during massaging thereof.

2. Description of the Related Art

In the past, it has been known to apply chemotherapeutic, antibiotic, or other medicinal agents to the gum areas of patients suffering from gingivitis or periodontal disease. Many patients who suffer from these diseases and other related gum disease are frequently required to stimulate the soft tissues of the gum by applying a rubber massage tip thereto, moving the tip across the gum surface in a massaging motion. The required therapy program, involving both the application of various medicaments as well as routine massaging of the gums is a rather complex and time-consuming task and is therefore often not performed in the required manner. Therefore, many patients suffering from gum disease do not get the optimum results from the prescribed regime. Consequently, there exists a need in the art for an improved method and device for treating gingivitis, periodontal disease, and other related gum diseases which is simple for a patient to use in a daily prescribed regime and which is as effective as therapy administered by a dental practitioner.

SUMMARY OF THE INVENTION

The present invention is directed at providing a solution to the aforementioned longstanding problem which exists in the gum therapy field by providing a disposable gum massaging tip for use on a conventional handheld gum massaging tool, the disposable tip being specifically adapted to carry a medicament such that during use, the tip will massage the gums while simultaneously applying any of various prescribed medicaments to the gum area, thereby providing a direct means of topical treatment at the sight of gum disease.

It is, therefore, an important object of the present invention to provide a substantially conical shaped disposable massage tip adapted for attachment with a conventional handheld gum massage tool which during use, acts to both stimulate the gums while simultaneously applying any of various medicaments to the gum and tooth interface effectively combatting bacterial activity which, if left undisturbed, results in the formation of periodontal pockets or pocket pathology progression.

It is another object of the present invention to provide a disposable massage tip member which is relatively small in size and adapted to be removably attached to a conventional gum massage tool providing a direct means of topical treatment to the gum area during stimulation thereof using any of a number of prescribed medicaments.

It is still a further object of the present invention to provide a disposable gum massage tip member which is impregnated with any of various medicinal agents so as to greatly enhance the dental practitioner's ability to properly treat periodontal disease and other related gum diseases.

It is yet another object of the present invention to provide a disposable gum massage tip member which is adapted to carry one of a number of medicaments including prescribed antibiotics and other agents which are best suited to treat a specific stage or state of a specific gum disease, wherein a practitioner could prescribe an appropriate number of massage tips impregnated with the specific antibacterial agent for a treatment regime.

It is still a further object of the present invention to provide various embodiments of the gum massage tip of the present invention, wherein the medicament can be either impregnated within the tip or carried thereon for direct, topical application to the sight of gum disease during massaging of the gums.

Yet another object of the present invention is to provide a disposable gum massage tip which is adapted to carry a prescribed medicament and which can be removably attached to any conventionally known handheld instrument useful for massaging the gums including a motorized instrument or a manual massaging instrument such as a disposable stick or a reusable wand.

These and other objects, advantages, and novel features of the present invention will become more readily apparent from the description which follows.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
FIG. 1 is a side elevational view illustrating the massage tip member of the present invention attached to the distal end of a conventional handheld gum massaging tool.
Figure 2:
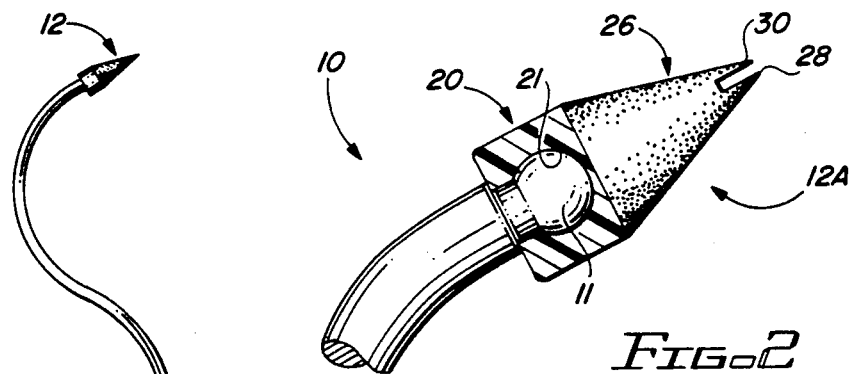
FIG. 2 is a cross-sectional view of one embodiment of the present invention.
Figure 3:
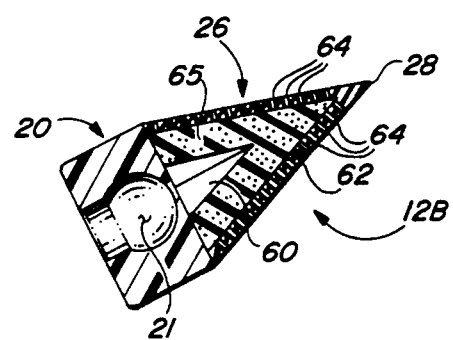
FIG. 3 is a cross-sectional view of an alternative embodiment of the present invention.
Figure 4:
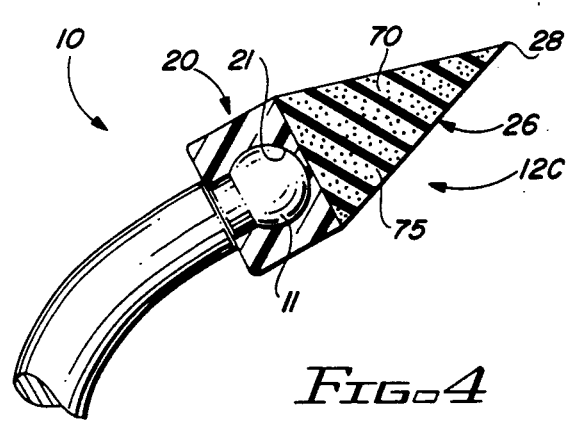
FIG. 4 is a cross-sectional view of still another alternative embodiment of the present invention.

Referring to the drawings, FIG. 1 illustrates a handheld gum massage wand 10, wherein a disposable, substantially conical-shaped medicinal applicator and massage tip member 12 of the present invention is adapted to be removably attached to a distal end thereof. The disposable tip member 12 can be one of generally three preferred embodiments 12A, 12B, 12C as illustrated in FIGS. 2-4. Each of the various embodiments 12A, 12B, 12C of the tip member contains a base portion 20 and an extending, generally conical or frusto-conical portion 26 terminating at a substantially pointed end 28. The wand 10 can be of a handheld type or of the type used in connection with a vibrating or other motorized instrument adapted to move the wand and attached tip portion in a generally massaging motion. The wand 10 preferably is of the type which includes a beaded end 11 which is sized to be snugly received within the tip member 12 at its base portion 20 thereof. The base portion 20 contains an annular groove 21 sized and configured for receipt of the bead element 11 therein so as to effectively secure the tip member 12 to the distal end of the wand 10.

Referring now to the first embodiment shown in FIG. 2, the tip member 12A of the first embodiment has an axially extending groove or notch 30 in which a medicame of any suitable type may be carried therein. It is preferred that the tip 12A be constructed of a rubber-like or other suitable, firm, yet resilient material. Various conventional materials are available on the market which are relatively soft, yet resilient enough to be utilized as a massaging, gum stimulating material. In use, the tip member of the first embodiment 12A is introduced onto the marginal cervical areas along the gum and tooth interface such that the gum tissues are stimulated while at the same time the medicament is topically applied to the gum tissues along the gum and tooth interface where initial gingivitis and periodontal disease occurs. As the distal end of a wand 10 is moved in a vibratory, side-to-side motion by the patient, the medicament carried in the notch 30 of the tip member 12A is effectively and evenly applied to the gums.

The second alternative embodiment clearly shown in FIG. 3 is directed to a massage tip member 12B which includes a rigid inner core 60 and an outer tip casing 62 comprising a semipermeable membrane having micropores 64 extending therethrough. The tip casing 62 is impregnated with a charge of medicament 65. The medicament 65 is of a particular chemical construction such that upon contact with salvia or other liquid, the medicament 65 dissolves and discharge is thereafter activated through, the micropores 64. The medicament 65 is thereby applied to the gums during massaging of the gums in a somewhat similar matter as described in the description of the first embodiment. As the tip member 12B is introduced to the gingival areas, saliva dissolves the medicament 65, allowing for the medicament 65 to be subsequently released through the micropores 64 so as to be effectively and easily applied to the gum tissues. The rigid inner core 62 provides for stability and support of the tip casing 62 during massaging engagement with the gum tissues.

The third alternative embodiment, depicted in FIG. 4, is directed to a disposable tip member 12C wherein the conical end portion 26 is formed of an absorbent, sponge material 70. The medicament 75 in this particular embodiment is preferably of a liquid type substance and is applied directly to the absorbent conical end portion 70 by dipping the tip member into a supply of the medicament, allowing the substance to be absorbed into the conical end portion 26. The tip member 12C, however, even though composed of a soft absorbent material 70, is still resilient enough to impart stimulation to the gums during vibratory, massaging action to the gums.

Figure 5:
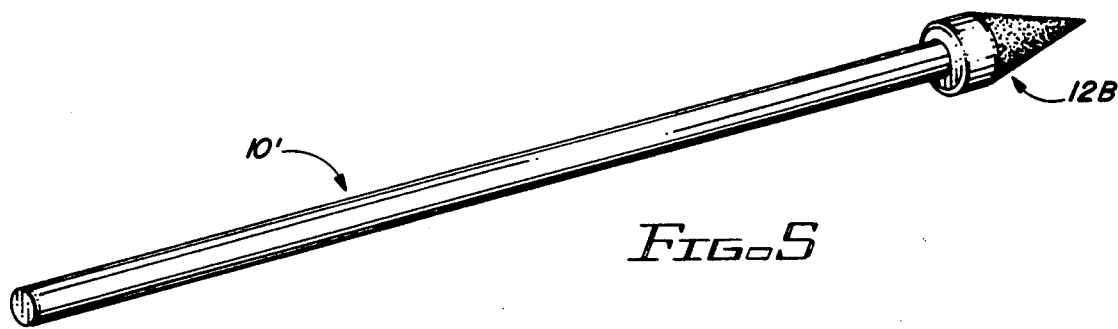
FIG. 5 is a perspective view illustrating the massage tip of the present invention attached to the distal end of a disposable stick.

Referring to FIG. 5, the tip member 12 is shown attached to a disposable stick 10: This particular embodiment illustrates a convenient method of prescribing tip members 12, and particular tip member 12B, which are impregnated with a prescribed medicament for treating a particular patient, wherein the tip member 12 and attached stick can be easily discarded after use. In this manner, the practitioner could prescribe a treatment wherein the patient would be given a certain number of sticks 10' and attached tips 12 for use to carry out the prescribed regime.

Therefore, in summary, the disposable tip members of all three embodiments are adapted for connection to the distal end of a conventional gum massage tool so that the various disposable tip members 12A, 12B, 12C will produce a massaging effect to the gum tissues while simultaneously applying a medicament thereto. The disposable tip members 12A, 12B, 12C physically carry a supply of a medicinal agent such that a prescribed dose of any particular agent can be applied to the gum areas as the gum tissues are stimulated. The present invention provides an accurate, convenient, and completely disposable means for direct topical treatment of the gums at the sight of gum disease.

While this invention has been described in what is considered to be a practical and preferred embodiment, it is recognized that departures may be made within the spirit and scope of this invention which is, therefore, not to be limited except as set forth in the claims hereinafter and within the doctrine of equivalents.

I claim:

1. A disposable massage tip member for use on a handheld dental tool or like elongate item for use in massaging the gums of the user, comprising:
   a base portion including attachment means for removable attachment to a distal end of the handheld tool or like elongate item,
   a substantially conical-shaped portion,
   said substantially conical-shaped portion including a rigid inner core and an outer semi-permeable membrane,
   said outer membrane including a plurality of micropores extending at least partially therethrough and in fluid communication with an inner membrane portion, and
   said inner membrane portion being impregnated with a dose of medicament wherein the medicament is adapted to be released through said micropores and onto the gums upon application of the tip member to the gums during massaging thereof, thereby providing an effective and accurate means of dispensing a specific quantity of the medicament for topical treatment to the gums.

2. The massage tip member of claim 1 wherein said medicament is of a chemical construction such that upon contact with saliva or other liquid, the medicament is dissolved and subsequently released through said micropores.

3. The massage tip member of claim 2 wherein the tip member is attached to a distal end of a disposable elongate stick wherein the tip member and said stick are to be discarded after use.

* * * * *